United States Patent
Matsuura (10) Patent No.: US 10,775,604 B2
(45) Date of Patent: Sep. 15, 2020

(54) OBJECTIVE OPTICAL SYSTEM FOR ENDOSCOPE

(71) Applicant: OLYMPUS CORPORATION, Hachioji-shi, Tokyo (JP)

(72) Inventor: Hiroto Matsuura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 184 days.

(21) Appl. No.: 16/142,324

(22) Filed: Sep. 26, 2018

(65) Prior Publication Data
US 2019/0025568 A1  Jan. 24, 2019

Related U.S. Application Data (63) Continuation of application No. PCT/JP2017/011309, filed on Mar. 22, 2017.

(30) Foreign Application Priority Data

Apr. 12, 2016  (JP) .................................. 2016-079697

(51) Int. Cl.
*G02B 9/60* (2006.01)
*G02B 23/24* (2006.01)
(Continued)

(52) U.S. Cl.
CPC ........ *G02B 23/243* (2013.01); *A61B 1/00096* (2013.01); *A61B 1/00188* (2013.01);
(Continued)

(58) Field of Classification Search
CPC .......... G02B 23/243; G02B 7/04; G02B 9/60; G02B 9/62; G02B 13/0045; G02B 13/04;
(Continued)

(56) References Cited

U.S. PATENT DOCUMENTS

2008/0180809 A1* 7/2008 Igarashi ............. G02B 23/2438
359/689
2012/0057251 A1  3/2012 Takato
(Continued)

FOREIGN PATENT DOCUMENTS

JP  1934233 B2  5/2012
WO  2011070930 A1  6/2011
(Continued)

OTHER PUBLICATIONS

International Search Report (ISR) dated Jun. 20, 2017 issued in International Application No. PCT/JP2017/011309.
Written Opinion dated Jun. 20, 2017 issued in International Application No. PCT/JP2017/011309.
International Preliminary Report on Patentability (IPRP) and Written Opinion dated Oct. 16, 2018 issued in International Application No. PCT/JP2017/011309.

*Primary Examiner* — Alicia M Harrington
(74) *Attorney, Agent, or Firm* — Holtz, Holtz & Volek PC

(57) ABSTRACT

An objective optical system for endoscope consists of, in order from an object side, a first negative lens L1 which is planoconcave, and of which a flat surface is directed toward the object side, a second meniscus lens L2 having a convex surface directed toward an image side, a third positive meniscus lens L3 having a convex surface directed toward the object side, a fourth positive lens L4, and a cemented lens in which fifth positive lens L5 and a sixth negative lens L6 are cemented. Focusing is carried out by the third positive meniscus lens moving along an optical axis AX, and the following conditional expressions (1-1) and (1-2) are satisfied:

$$0.41 < |f_{lp}/f_2| < 1 \quad (1\text{-}1), \text{ and}$$

$$0.55 < d_{45}/f_{lp} < 1 \quad (1\text{-}2).$$

7 Claims, 7 Drawing Sheets

(51) Int. Cl.
  *G02B 27/00* (2006.01)
  *G02B 9/62* (2006.01)
  *G02B 13/00* (2006.01)
  *G02B 13/04* (2006.01)
  *A61B 1/00* (2006.01)
  *G02B 7/04* (2006.01)

(52) U.S. Cl.
  CPC .............. *G02B 7/04* (2013.01); *G02B 9/60* (2013.01); *G02B 9/62* (2013.01); *G02B 13/0045* (2013.01); *G02B 13/04* (2013.01); *G02B 23/2407* (2013.01); *G02B 27/0025* (2013.01)

(58) Field of Classification Search
  CPC ............ G02B 23/2407; G02B 27/0025; A61B 1/00096; A61B 1/00188
  See application file for complete search history.

(56) References Cited

U.S. PATENT DOCUMENTS

| | | |
|---|---|---|
| 2013/0155212 A1 | 6/2013 | Kamo |
| 2013/0217965 A1 | 8/2013 | Sasamoto |
| 2016/0238832 A1 | 8/2016 | Sasamoto |
| 2016/0327780 A1 | 11/2016 | Kamo et al. |

FOREIGN PATENT DOCUMENTS

| | | |
|---|---|---|
| WO | 2012169369 A1 | 12/2012 |
| WO | 2013021744 A1 | 2/2013 |
| WO | 2015064614 A1 | 5/2015 |
| WO | 2015194311 A1 | 12/2015 |

\* cited by examiner

OBJECTIVE OPTICAL SYSTEM FOR ENDOSCOPE

CROSS-REFERENCE TO RELATED APPLICATION

The present application is a continuation application of PCT/JP2017/011309 filed on Mar. 22, 2017 which is based upon and claims the benefit of priority from Japanese Patent Application No. 2016-079697 filed on Apr. 12, 2016; the entire contents of which are incorporated herein by reference.

BACKGROUND OF THE INVENTION

Field of the Invention

The present invention relates to an objective optical system for endoscope such as an objective optical system for endoscope used in a field such as a medical field and an industrial field.

Description of the Related Art

An endoscope is an apparatus that has been used widely in the medical field and the industrial field. In the medical field, images of various parts in a body cavity are achieved by an endoscope inserted into the body cavity. Diagnosis of an observed part is carried out by using these images. In such manner, endoscopes are used for observation and diagnosis of various parts in a body cavity. Moreover, for the observation, it is preferable that the observation can be carried out by an adequate brightness and adequate resolution.

Furthermore, in a case of observing from a near-point object up to a far-point object inside the body cavity, it is preferable to have an observation depth which does not pose a problem. For fulfilling these requirements, objective optical systems provided with a focusing function (hereinafter, referred to as 'focusing optical system') have been proposed in recent years. Moreover, optical systems disclosed in International Unexamined Patent Application Publication No. 2013/021744, International Unexamined Patent Application Publication No. 2012/169369, Japanese Patent No. 4934233 Publication, and International Unexamined Patent Application Publication No. 2015/194311 are examples of the focusing optical system for endoscope.

In a focusing optical system, it is necessary to move a lens for focusing. Therefore, generally, an overall length of a focusing optical system tends to become larger than an outer diameter and an overall length of a fixed-focus optical system.

In recent years, small-sizing of objective optical systems has been desired. Therefore, an outer diameter and an overall length of an objective optical system becoming larger than the outer diameter and the overall length of the fixed-focus optical system cannot fulfil the requirements. For this reason, in a focusing optical system, it is necessary to make the overall length and the outer diameter small while an image quality is secured. As a means of achieving this, making an image pickup element small by making a size of one pixel of the image pickup element small and scaling down the focusing optical system may be cited. Here, scaling down the optical system refers to reducing various specification values such as a radius of curvature of a lens surface, a thickness, and an air space by multiple of coefficient.

Here, to secure the image quality, it is necessary not only to make the image pickup element small but also to secure a performance of the focusing optical system consistent with the small size of the image pickup element. A point image which is formed by an optical system has a spreading due to an effect of diffraction. When a pixel pitch is made small, a size of the point image becomes excessively large with respect to one pixel. Therefore, the point image is to be made small by making an Fno bright.

In such manner, when the pixel pitch is made small, if the Fno is not made bright, an MTF (Modulation Transfer Function) which is necessary cannot be secured. When it is not possible to secure the required MTF, even when the optical system is scaled down as it has been, a favorable optical performance cannot be secured. For such reason, an objective optical system in which the MTF is secured by making the Fno bright, and an aberration is corrected appropriately, is sought.

SUMMARY OF THE INVENTION

An objective optical system for endoscope according to at least some embodiments of the present invention consists of, in order from an object side:

a first negative lens which is planoconcave, and of which a flat surface is directed toward the object side, a second meniscus lens having a convex surface directed toward an image side, a third positive meniscus lens having a convex surface directed toward the object side, a fourth positive lens, and a cemented lens in which a fifth positive lens and a sixth negative lens are cemented, wherein focusing is carried out by the third positive meniscus lens moving along an optical axis, and the following conditional expressions (1-1) and (1-2) are satisfied:

$$0.41 < |f_{lp}/f_2| < 1 \quad (1\text{-}1), \text{ and}$$

$$0.55 < d_{45}/f_{lp} < 1 \quad (1\text{-}2)$$

where, $f_{lp}$ denotes a focal length of the fourth positive lens, $f_2$ denotes a focal length of the second meniscus lens, and $d_{45}$ denotes an air space between the fourth positive lens and the fifth positive lens.

DETAILED DESCRIPTION OF THE INVENTION

Reasons for and an effect of adopting such arrangements for an objective optical system for endoscope according to the present embodiment will be described below by using the accompanying diagrams. However, the present invention is not restricted to the embodiment described below.

Figure 1A:
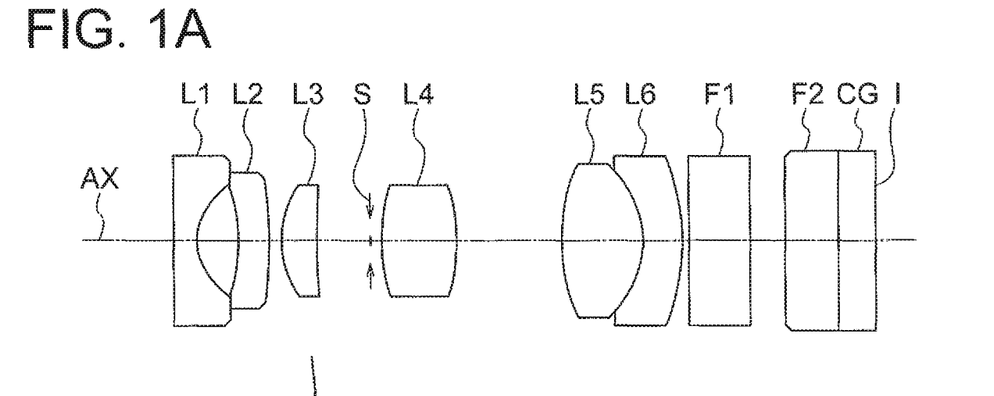
FIG. 1A and FIG. 1B are cross-sectional views showing lens arrangements of an objective optical system for endoscope according to the present embodiment.
Figure 1B:
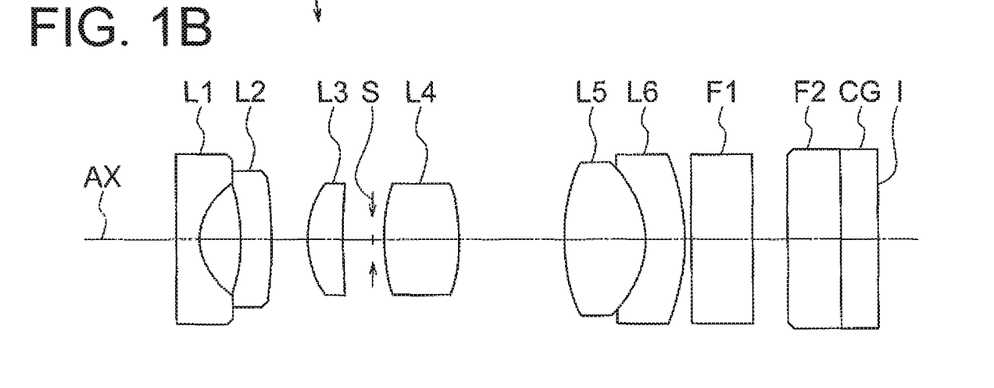

FIG. 1A and FIG. 1B are cross-sectional views showing a lens arrangement of the objective optical system for endoscope according to the present embodiment. Here, FIG. 1A is a cross-sectional view showing a lens arrangement of the objective optical system for endoscope in a normal observation state, and FIG. 1B is a cross-sectional view showing a lens arrangement of the objective optical system for endoscope in a close observation state.

The objective optical system for endoscope according to the embodiment includes in order from an object side, a first negative lens L1 which is planoconcave, and of which a flat surface is directed toward the object side, a second meniscus lens L2 having a convex surface directed toward an image side, a third positive meniscus lens L3 having a convex surface directed toward the object side, an aperture stop S, a fourth positive lens L4, and a cemented lens in which a fifth positive lens L5 and a sixth negative lens L6 are cemented, wherein focusing is carried out by the third positive meniscus lens L3 moving along an optical axis, and the following conditional expressions (1-1) and (1-2) are satisfied:

$$0.41 < |flp/f_2| < 1 \quad (1\text{-}1), \text{ and}$$

$$0.55 < d_{45}/flp < 1 \quad (1\text{-}2)$$

where, flp denotes a focal length of the fourth positive lens L4, $f_2$ denotes a focal length of the second meniscus lens L2, and $d_{45}$ denotes an air space between the fourth positive lens L4 and the fifth positive lens L5.

Moreover, it is more preferable that conditional expression (1-1) and conditional expression (1-2) be satisfied simultaneously.

Furthermore, an infra-red cut filter F1, a cover glass F2, and a CCD (charge coupled device) cover glass CG are disposed on the image side of the cemented lens.

Reasons for and effect of adopting such arrangement in the present embodiment will be described below.

It is necessary to form an objective optical system having a high performance and a small size for using in an endoscope. For this, firstly, the first negative lens L1 which is planoconcave, and of which a flat surface is directed toward the object side is disposed nearest to object of the objective optical system for endoscope. Accordingly, it is possible to let an arrangement to be a retro-focus arrangement. Furthermore, in view of usage conditions of an endoscope, by letting the shape to be planoconcave, it is possible to make water removal during the observation favorable as well as to reduce cracking of lens due to an impact.

Moreover, the second meniscus lens L2 having the convex surface directed toward the image side is disposed on the image side of the first negative lens L1. Accordingly, a lens diameter is suppressed from becoming large while correcting an aberration due to the first negative lens L1.

A focusing lens group, in which a lens moves, is disposed on the image side of the second meniscus lens L2. The focusing lens group includes the third positive meniscus lens L3 having the convex surface directed toward the object side. Accordingly, it is possible to suppress an aberration fluctuation due to focusing.

The fourth positive lens L4 having a positive refractive power is disposed on the image side of the third positive meniscus lens L3, and furthermore, the cemented lens of the fifth positive lens L5 and the sixth negative lens L6 is disposed on the image side of the fourth positive lens L4, thereby correcting a chromatic aberration. In such lens arrangement, for small-sizing of the optical system, when a height of a light ray at the first negative lens L1 is to be suppressed to be small, it is necessary to make a focal length of the fourth positive lens L4 small, or in other words, to make the refractive power large.

However, as a result of this, aberrations including a spherical aberration become substantial, and a balance of aberration correction of the overall optical system is deteriorated.

For such reason, in the objective optical system for endoscope of the present embodiment, for keeping a balance of the aberration correction, it is preferable that the following conditional expression (1-1) and conditional expression (1-2) be satisfied, and more preferably, be satisfied simultaneously:

$$0.41 < |flp/f_2| < 1 \quad (1\text{-}1), \text{ and}$$

$$0.55 < d_{45}/flp < 1 \quad (1\text{-}2)$$

where, flp denotes a focal length of the fourth positive lens L4, $f_2$ denotes a focal length of the second meniscus lens L2, and $d_{45}$ denotes an air space between the fourth positive lens L4 and the fifth positive lens L5.

Conditional expression (1-1) is related to a ratio of flp and $f_2$. Conditional expression (1-2) is related to a ratio of $d_{45}$ and flp. When a value exceeds an upper limit value of conditional expression (1-1), the spherical aberration becomes excessively large, and it is not possible to keep the balance of aberration correction.

When the value falls below a lower limit value of conditional expression (1-1), a curvature of field becomes excessively large, and it is not possible to keep the balance of aberration correction.

When a value exceeds an upper limit value of conditional expression (1-2), a longitudinal chromatic aberration becomes excessively large, and it is not possible to keep the balance of aberration correction.

When the value falls below a lower limit value of conditional expression (1-2), the spherical aberration becomes excessively large, and it is not possible to keep the balance of aberration correction.

By satisfying conditional expressions (1-1) and (1-2), it is possible to carry out an appropriate aberration correction, and to suppress the height of a light ray passing through the first negative lens L1 while securing an optical performance, showing an effect that it is possible to make an outer diameter small.

Moreover, in this lens arrangement, the cemented lens corrects a chromatic aberration of magnification occurred at the first negative lens L1. An appropriate glass material is set for the fifth positive lens L5 in the cemented lens, in combination with the sixth negative lens L6 that is cemented for correcting the chromatic aberration of magnification.

When the refractive power of the fifth positive lens L5 is made excessively large by changing a radius of curvature or a thickness, it is necessary to suppress the positive refractive power of the fourth positive lens L4 immediately before the object side for keeping the balance of aberration.

Therefore, an appropriate setting of the refractive power of the fourth positive lens and the cemented lens becomes necessary.

For such reason, in the objective optical system for endoscope of the present embodiment, it is preferable that the following conditional expression (2) be satisfied:

$$2.6 < f_{56}/flp < 3.8 \qquad (2)$$

where, flp denotes the focal length of the fourth positive lens L4, and $f_{56}$ denotes a focal length of the cemented lens.

Conditional expression (2) is related to a ratio of $f_{56}$ and flp. When a value exceeds an upper limit value of conditional expression (2), it becomes difficult to correct the chromatic aberration of magnification adequately.

When the value falls below a lower limit value of conditional expression (2), either the spherical aberration is deteriorated or correction of the chromatic aberration of magnification becomes excessive. By satisfying conditional expression (2), an appropriate aberration correction is possible for a problem of an aberration that is accompanied by the small-sizing of the optical system, showing an effect that it is possible secure the optical performance.

Moreover, in this lens arrangement, the first negative lens L1 forms a retro-focus arrangement with a large negative refractive power. A substantial aberration occurs at the first negative lens L1. Therefore, it becomes significant to let the fourth positive lens L4 have a large positive refractive power.

For such reason, in the objective optical system for endoscope according to the present embodiment, it is preferable that the following conditional expression (3) be satisfied:

$$4.1 < \Sigma d/flp < 5.5 \qquad (3)$$

where, flp denotes the focal length of the fourth positive lens L4, and $\Sigma d$ denotes an overall optical length of the objective optical system for endoscope.

Conditional expression (3) is related to a ratio of $\Sigma d$ and flp. When a value exceeds an upper limit value of conditional expression (3), the longitudinal chromatic aberration is deteriorated.

When the value falls below a lower limit value of conditional expression (3), the refractive power of the fourth positive lens L4 becomes large, and the spherical aberration is deteriorated, thereby degrading the balance of aberration correction.

By satisfying conditional expression (3), an appropriate aberration correction is possible for a problem of an aberration that is accompanied by the small-sizing of the optical system, showing an effect that it is possible to secure the optical performance.

Moreover, in this lens arrangement, a balance of the refractive power of the fourth positive lens L4 and the thickness of the fourth positive lens L4 becomes significant for suppressing the light-ray height at the first negative lens L1.

For such reason, in the objective optical system for endoscope according to the present embodiment, it is preferable that the following conditional expression (4) be satisfied:

$$0.44 < d_4/flp < 1 \qquad (4)$$

where, flp denotes the focal length of the fourth positive lens L4, and $d_4$ denotes a thickness of the fourth positive lens L4.

Conditional expression (4) is related to a ratio of $d_4$ and flp. When a value exceeds an upper limit value of conditional expression (4), a coma is deteriorated.

When the value falls below a lower limit value of conditional expression (4), the refractive power of the fourth positive lens L4 becomes small, and the spherical aberration is deteriorated, thereby degrading the balance of the aberration correction. Therefore, by satisfying conditional expression (4), an appropriate aberration correction is possible for a problem of an aberration that is accompanied by the small-sizing of the optical system, showing an effect that it is possible to secure the optical performance.

Moreover, there is a tendency to make the size of the image pickup element small by making the size of one pixel of the image pickup element small. In a situation of making the size of one pixel small, it is necessary to suppress the maximum light-ray height at the first negative lens L1, to make the outer diameter small, and to make the Fno small, thereby securing the optical performance.

For such reason, in the objective optical system for endoscope of the present embodiment, it is preferable that the following conditional expression (5) be satisfied:

$$1.8 < flp \times rh_1/ih^2 < 2.5 \qquad (5)$$

where, flp denotes the focal length of the fourth positive lens L4, $rh_1$ denotes the maximum height of a light ray in a normal observation state of the first negative lens L1, and ih denotes an image height.

Conditional expression (5) is related to an appropriate relationship of flp, $rh_1$, and ih. When a value exceeds an upper limit value of conditional expression (5), the light-ray height at the first negative lens L1 becomes high.

When the value falls below a lower limit value of conditional expression (5), the positive refractive power of the fourth positive lens L4 becomes large, and the balance of aberration correction is degraded. Therefore, by satisfying conditional expression (5), it is possible to carry out an appropriate aberration correction, and to suppress the height of the light ray passing through the first negative lens L1 while securing the optical performance, showing an effect that it is possible to make the outer diameter small.

Moreover, in this lens arrangement, a balance of the negative refractive power of the lens group on the object side and the positive refractive power of the lens group on the image side, sandwiching the aperture stop S, becomes significant for keeping the balance of the aberration correction while suppressing the light-ray height at the first negative lens L1.

For such reason, in the objective optical system for endoscope of the present embodiment, it is preferable that the following conditional expression (6) be satisfied:

$$1 < |flp \times f_{123}|/rh_1^2 < 2.1 \qquad (6)$$

where, flp denotes the focal length of the fourth positive lens L4, $rh_1$ denotes the maximum height of a light ray in the normal observation state of the first negative lens L1, and $f_{123}$ denotes a combined focal length in the normal observation state of the first negative lens L1, the second meniscus lens L2, and the third positive meniscus lens L3.

Conditional expression (6) is related to an appropriate relationship of flp and $f_{123}$. When a value exceeds an upper limit value of conditional expression (6), aberrations such as the coma and the longitudinal chromatic aberration are deteriorated.

When the value falls below a lower limit value of conditional expression (6), the light-ray height at the first negative lens L1 becomes high and either the outer diameter becomes large or the balance of aberration correction is degraded.

By satisfying conditional expression (6), it is possible to carryout appropriate aberration correction, and to suppress the height of the light ray passing through the first negative lens L1 while securing the optical performance, showing an effect that it is possible to make the outer diameter small.

Moreover, in this lens arrangement, it becomes significant to keep a balance of the refractive power of the overall optical system and the refractive power of the fourth positive lens L4 while suppressing the height of the light ray passing through the first negative lens L1, and making the outer diameter small.

For such reason, in the objective optical system for endoscope of the present embodiment, it is preferable that the following conditional expression (7) be satisfied:

$$1.76 < flp \times rh_1 / f1\_f^2 < 2.51 \quad (7)$$

where, flp denotes the focal length of the fourth positive lens L4, $rh_1$ denotes the maximum height of a light ray in the normal observation state of the first negative lens L1, and f1_f denotes a focal length of the overall objective optical system for endoscope in the normal observation state.

Conditional expression (7) is related to flp, $rh_1$, and f1_f. When a value exceeds an upper limit value of conditional expression (7), either an aberration such as the spherical aberration is deteriorated or the outer diameter becomes large.

When the value falls below a lower limit value of conditional expression (7), either an overall balance of aberration is disrupted or the light-ray height at the first negative lens L1 becomes high, and the outer dimeter becomes large.

By satisfying conditional expression (7), it is possible carry out an appropriate aberration correction, and to suppress the height of the light ray passing through the first negative lens L1 while securing the optical performance, showing an effect that it is possible to make the outer diameter small.

Examples will be described below.

Example 1

An objective optical system for endoscope according to an example 1 will be described below.

Figure 2A:
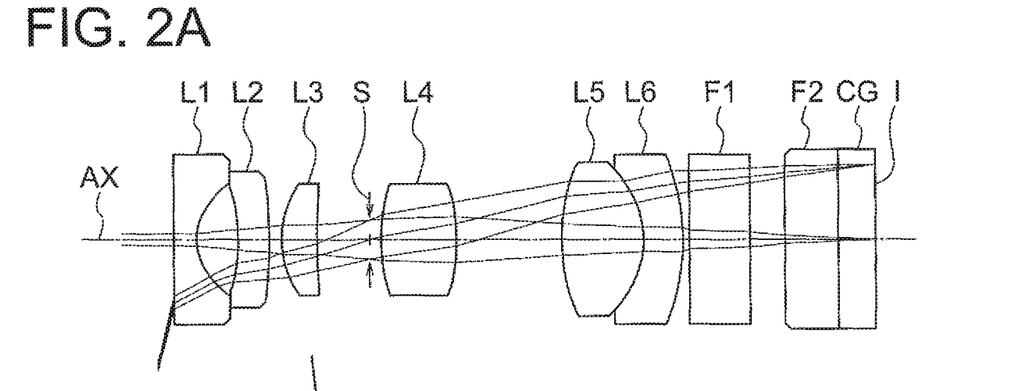
FIG. 2A and FIG. 2B are cross-sectional views showing lens arrangements of an objective optical system for endoscope according to an example 1.
Figure 2B:
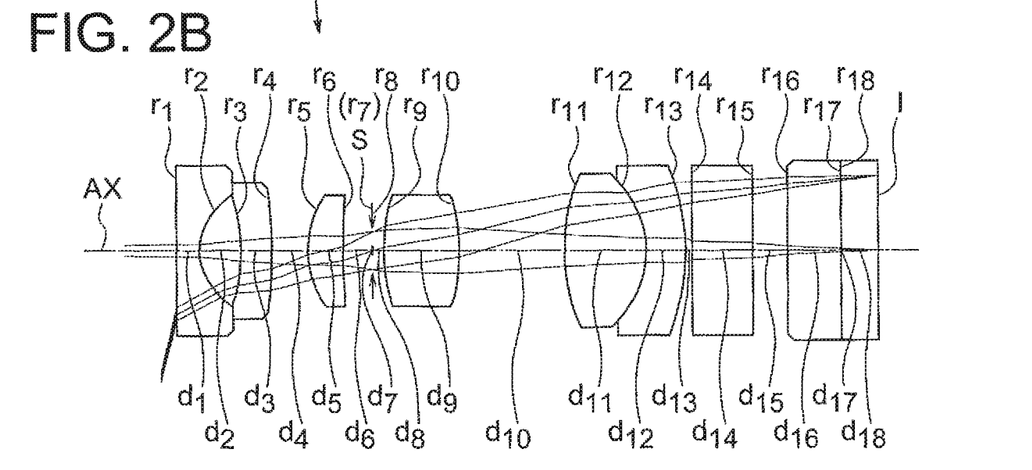
Figures 3A, 3B:
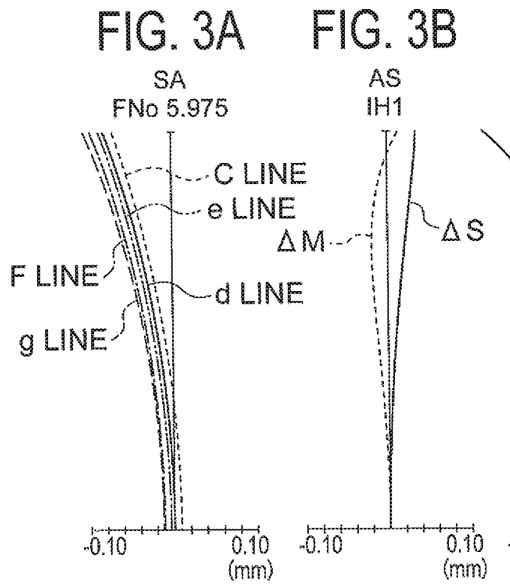
FIG. 3A, FIG. 3B, FIG. 3C, FIG. 3D, FIG. 3E, FIG. 3F, FIG. 3G, and FIG. 3H are aberration diagrams of the objective optical system for endoscope according to the example 1.
Figure 3C:
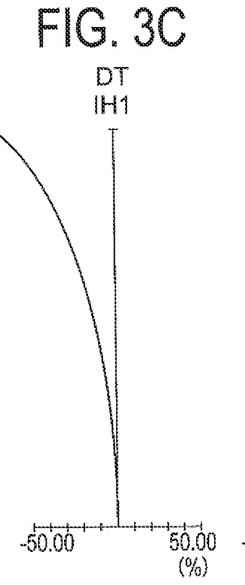
Figure 3D:
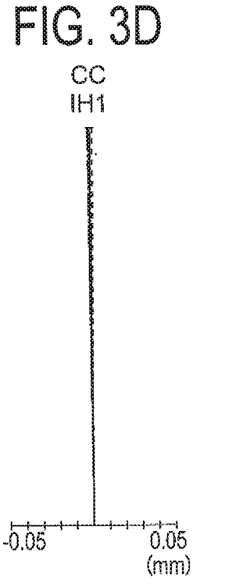
Figure 3E:
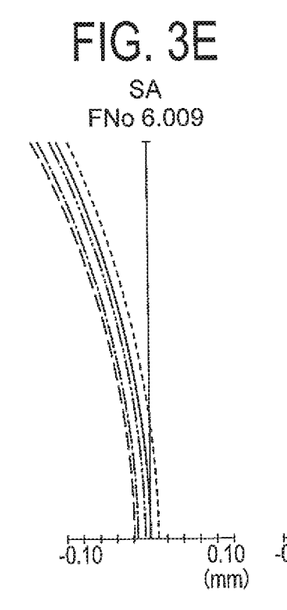
Figures 3F, 3G:
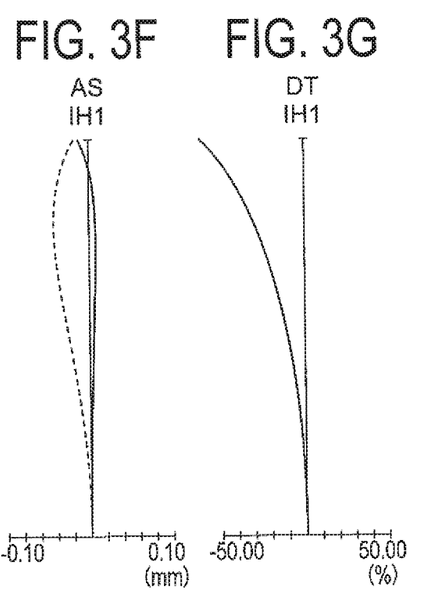
Figure 3H:
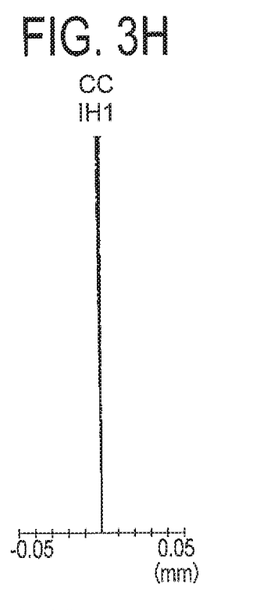

FIG. 2A is a lens cross-sectional view of the objective optical system for endoscope according to the present example in a normal observation state (an object point at a long distance), and FIG. 2B is a lens cross-sectional view of the objective optical system for endoscope according to the present example in a close observation state (an object point at a close distance).

In the example 1, the objective optical system for endoscope includes in order from an object side, a first negative lens L1 which is planoconcave, and of which a flat surface is directed toward the object side, a second negative meniscus lens L2 having a convex surface directed toward an image side, a third positive meniscus lens L3 having a convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red cut filter F1, a cover glass F2, and a CCD cover glass CG. The fifth positive lens L5 and the sixth negative meniscus lens L6 are cemented. Moreover, the cover glass F2 and the CCD cover glass CG are cemented.

A YAG (yttrium aluminum garnet) laser cut coating is applied to an object side of the infra-red cut filter F1 and an LD laser cut coating is applied to an image side of the infra-red cut filter F1. Moreover, the third positive meniscus lens L3 moves toward the image side (toward an image plane I) at the time of focusing from the normal observation state (FIG. 2A) to the close observation state (FIG. 2B).

FIG. 3A, FIG. 3B, FIG. 3C, and FIG. 3D show a spherical aberration (SA), an astigmatism (AS), a distortion (DT), and a chromatic aberration of magnification (CC) in the normal observation state of the present example.

FIG. 3E, FIG. 3F, FIG. 3G, and FIG. 3H show a spherical aberration (SA), an astigmatism (AS), a distortion (DT), and a chromatic aberration of magnification (CC) in the close observation state of the present example.

The various aberration diagrams indicate aberration for wavelengths of 656.27 nm (C-line), 587.56 nm (d-line), 486.13 nm (F-line), 435.83 nm (g-line), and 546.07 nm (e-line). Moreover, in each diagram, 'IH' denotes the maximum image height. Similar is true for other aberration diagrams described below.

Example 2

An objective optical system for endoscope according to an example 2 will be described below.

Figure 4A:
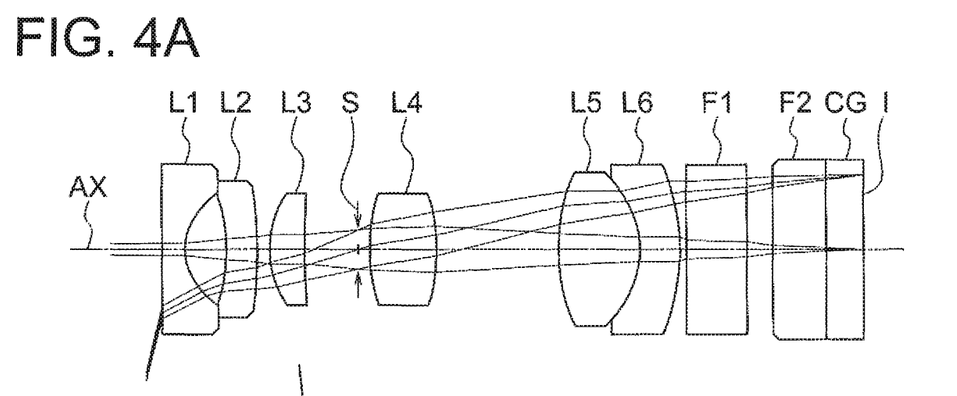
FIG. 4A and FIG. 4B are cross-sectional views showing lens arrangements of an objective optical system for endoscope according to an example 2.
Figure 4B:
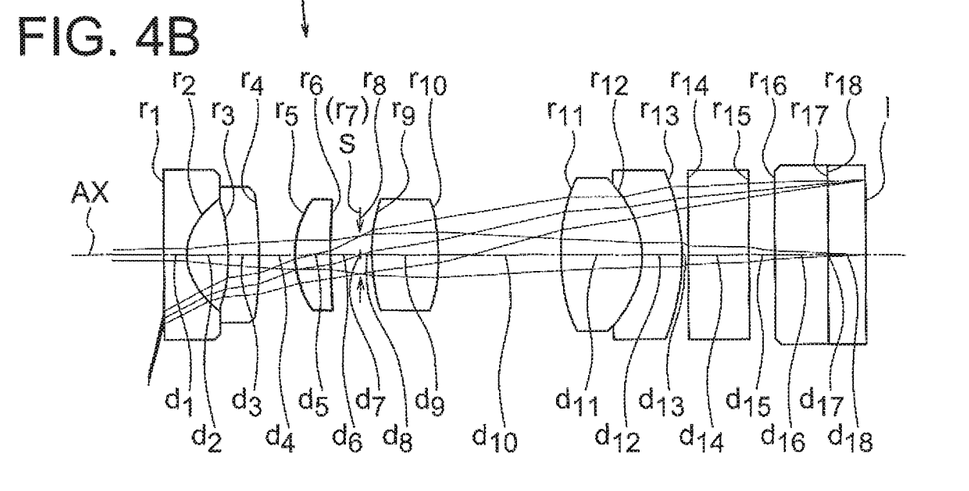
Figure 5A:
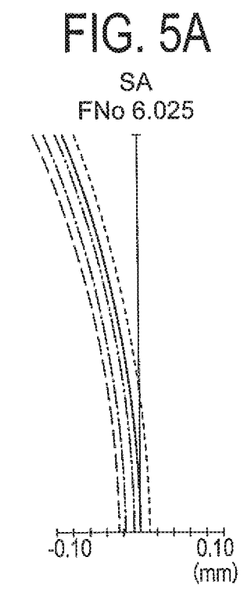
FIG. 5A, FIG. 5B, FIG. 5C, FIG. 5D, FIG. 5E, FIG. 5F, FIG. 5G, and FIG. 5H are aberration diagrams of the objective optical system for endoscope according to the example 2.
Figure 5B:
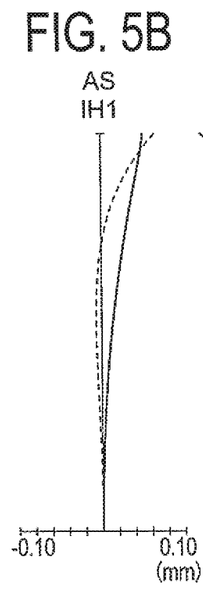
Figure 5C:
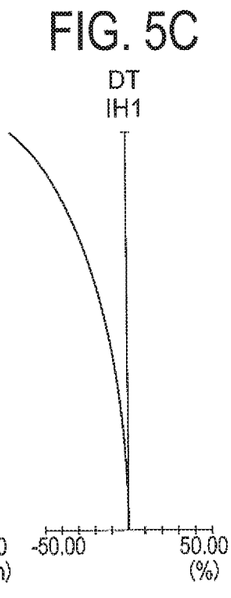
Figure 5D:
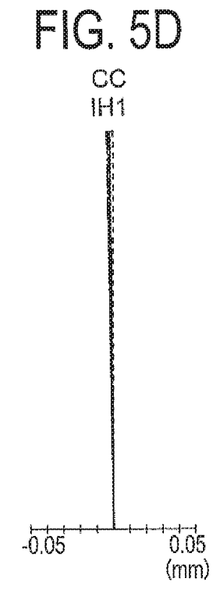
Figure 5E:
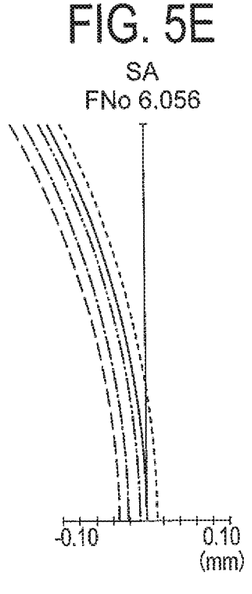
Figure 5F:
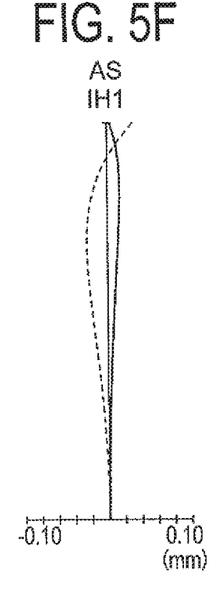
Figure 5G:
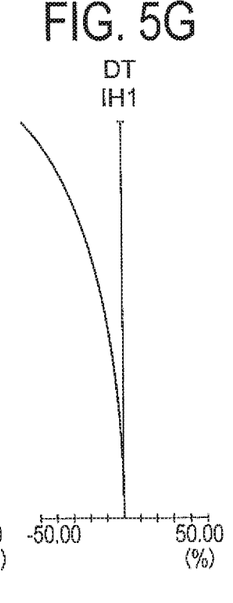
Figure 5H:
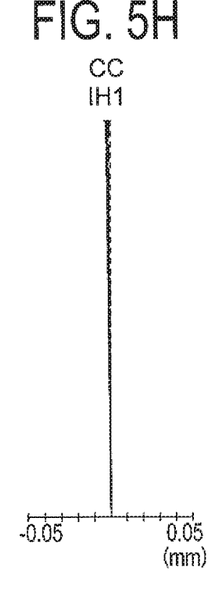

FIG. 4A is a lens cross-sectional view of the objective optical system for endoscope according to the present example in a normal observation state (an object point at a long distance), and FIG. 4B is a lens cross-sectional view of the objective optical system for endoscope according to the present example in a close observation state (an object point at a close distance).

In the example 2, similarly as in the example 1, the objective optical system for endoscope includes in order from an object side, a first negative lens L1 which is planoconcave, and of which a flat surface is directed toward the object side, a second negative meniscus lens L2 having a convex surface directed toward an image side, a third positive meniscus lens L3 having a convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red cut filter F1, a cover glass F2, and a CCD cover glass CG. The fifth positive lens L5 and the sixth negative meniscus lens L6 are cemented. Moreover, the cover glass F2 and the CCD cover glass CG are cemented.

A YAG laser cut coating is applied to an object side of the infra-red cut filter F1 and an LD laser cut coating is applied to an image side of the infra-red cut filter F1. Moreover, the third positive meniscus lens L3 moves toward the image side (toward an image plane I) at the time of focusing from the normal observation state (FIG. 4A) to the close observation state (FIG. 4B).

FIG. 5A, FIG. 5B, FIG. 5C, and FIG. 5D show a spherical aberration (SA), an astigmatism (AS), a distortion (DT), and a chromatic aberration of magnification (CC) in the normal observation state of the present example.

FIG. 5E, FIG. 5F, FIG. 5G, and FIG. 5H show a spherical aberration (SA), an astigmatism (AS), a distortion (DT), and a chromatic aberration of magnification (CC) in the close observation state of the present example.

Example 3

An objective optical system for endoscope according to an example 3 will be described below.

Figure 6A:
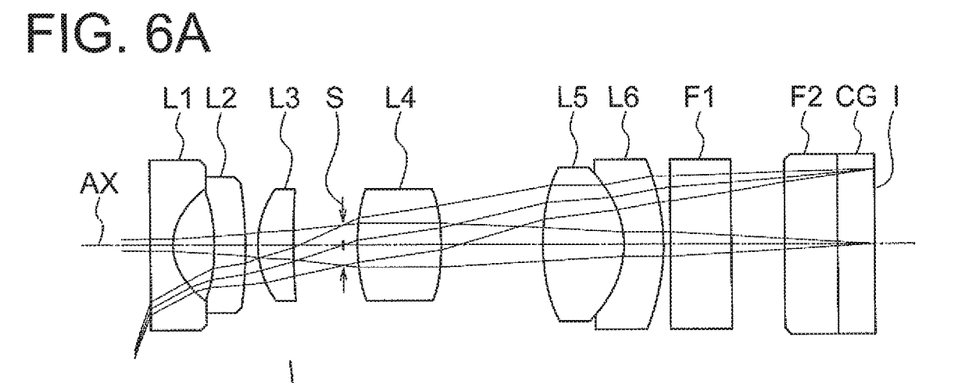
FIG. 6A and FIG. 6B are cross-sectional views showing lens arrangements of an objective optical system for endoscope according to an example 3.
Figure 6B:
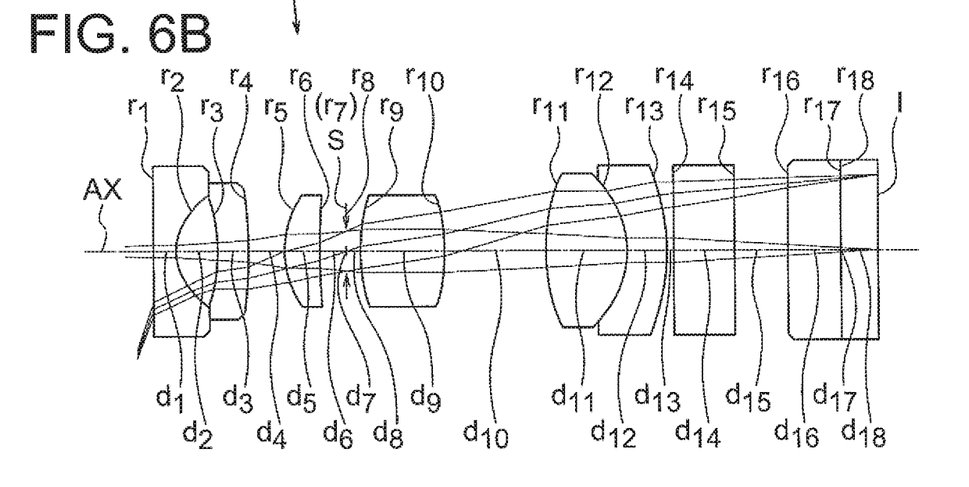
Figure 7A:
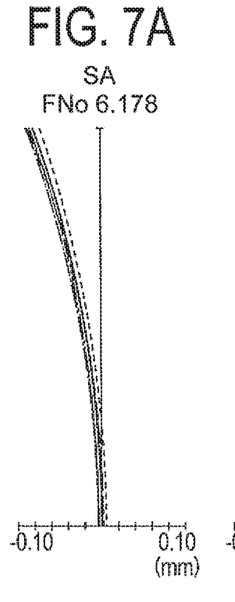
FIG. 7A, FIG. 7B, FIG. 7C, FIG. 7D, FIG. 7E, FIG. 7F, FIG. 7G, and FIG. 7H are aberration diagrams of the objective optical system for endoscope according to the example 3.
Figures 7B, 7C:
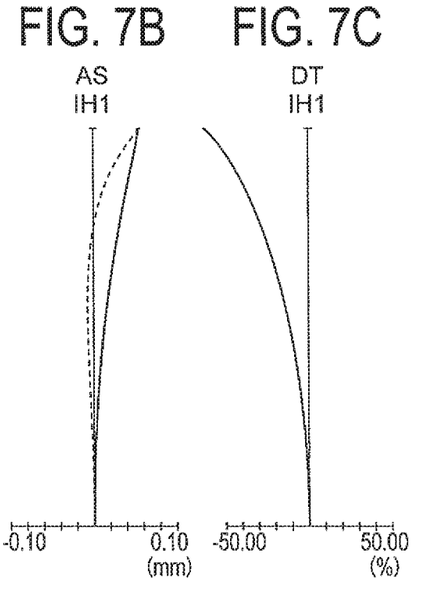
Figure 7D:
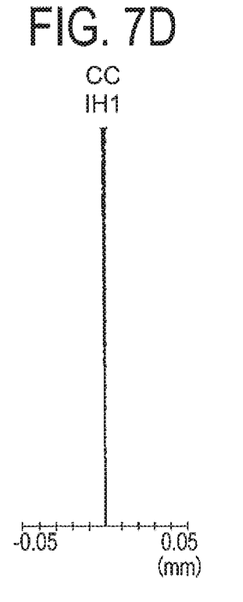
Figure 7E:
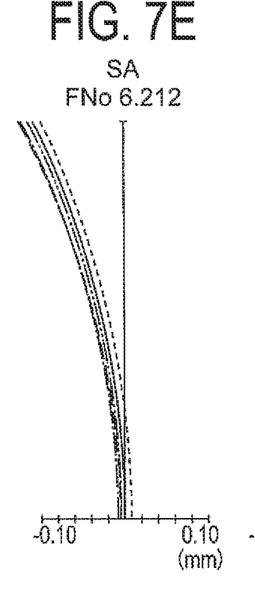
Figures 7F, 7G:
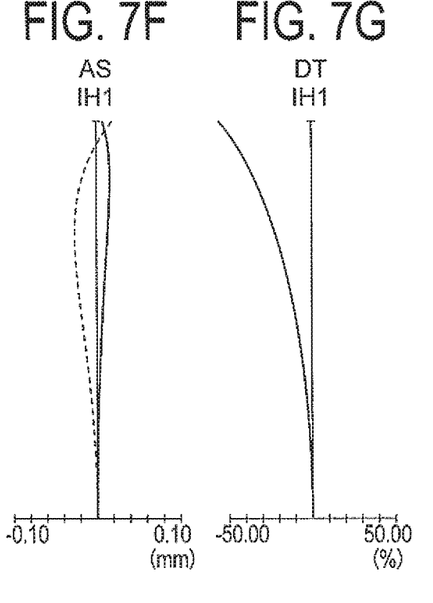
Figure 7H:
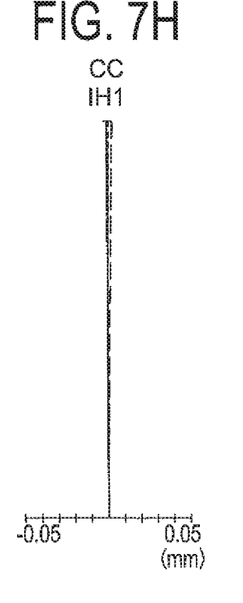

FIG. 6A is a lens cross-sectional view of the objective optical system for endoscope according to the present example in a normal observation state (an object point at a long distance), and FIG. 6B is a lens cross-sectional view of the objective optical system for endoscope according to the present example in a close observation state (an object point at a close distance).

In the example 3, similarly as in the example 1, the objective optical system for endoscope includes in order from an object side, a first negative lens L1 which is planoconcave, and of which a flat surface is directed toward the object side, a second negative meniscus lens L2 having a convex surface directed toward an image side, a third positive meniscus lens L3 having aa convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red cut filter F1, a cover glass F2, and a CCD cover glass CG. The fifth positive lens L5 and the sixth negative meniscus lens L6 are cemented. Moreover, the cover glass F2 and the CCD cover glass CG are cemented.

A YAG laser cut coating is applied to an object side of the infra-red cut filter F1 and an LD laser cut coating is applied to an image side of the infra-red cut filter F1. Moreover, the third positive meniscus lens L3 moves toward the image side (toward an image plane I) at the time of focusing from the normal observation state (FIG. 6A) to the close observation state (FIG. 6B).

FIG. 7A, FIG. 7B, FIG. 7C, and FIG. 7D show a spherical aberration (SA), an astigmatism (AS), a distortion (DT), and a chromatic aberration of magnification (CC) in the normal observation state of the present example.

FIG. 7E, FIG. 7F, FIG. 7G, and FIG. 7H show a spherical aberration (SA), an astigmatism (AS), a distortion (DT), and a chromatic aberration of magnification (CC) in the close observation state of the present example.

Numerical data of each example described above is shown below. In symbols, r denotes radius of curvature of each lens surface, d denotes a distance between respective lens surfaces, nd denotes a refractive index of each lens for a d-line, vd denotes an Abbe number for each lens, FNO. denotes an F number, ω denotes a half angle of view, IH denotes an image height, and f denotes a focal length of the entire system. BF denotes a back focus, LTL (=Σd) denotes an overall length of the optical system. The back focus is a unit which is expressed upon air conversion of a distance from a rearmost lens surface to a paraxial image surface. The overall length is a distance (not subjected to air conversion) from a lens surface nearest to object up to an optical surface nearest to image, and is a value which is constant in the normal observation state and the close observation state.

Example 1

Unit mm

Surface data

| Surface no. | r | d | nd | vd |
|---|---|---|---|---|
| 1 | ∞ | 0.3 | 1.883 | 40.76 |
| 2 | 0.84 | 0.55 | | |
| 3 | −2.339 | 0.42 | 1.883 | 40.76 |
| 4 | −5.702 | Variable | | |
| 5 | 1.354 | 0.46 | 1.58913 | 61.14 |
| 6 | 1.581 | Variable | | |
| 7(Stop) | ∞ | 0.03 | | |
| 8 | ∞ | 0.15 | | |
| 9 | 2.96 | 1 | 1.7725 | 49.60 |
| 10 | −2.96 | 1.4 | | |
| 11 | 2.439 | 1.1 | 1.48749 | 70.23 |
| 12 | −1.322 | 0.52 | 1.95906 | 17.47 |
| 13 | −3.071 | 0.09 | | |
| 14 | ∞ | 0.8 | 1.521 | 65.13 |
| 15 | ∞ | 0.4859 | | |
| 16 | ∞ | 0.7 | 1.51633 | 64.14 |
| 17 | ∞ | 0.01 | 1.513 | 64.00 |
| 18 | ∞ | 0.5 | 1.61062 | 50.49 |
| Image plane | ∞ | | | |

Variable data

| | Normal observation state | Close observation state |
|---|---|---|
| d4 | 0.16 | 0.49 |
| d6 | 0.7 | 0.37 |
| Fno | 5.975 | 6.009 |
| ω | 75.68 | 72.06 |
| IH | 1 | 1 |
| f | 0.997 | 0.999 |
| BF | −0.030 | −0.128 |
| LTL | 9.376 | |

Example 2

Unit mm

Surface data

| Surface no. | r | d | nd | vd |
|---|---|---|---|---|
| 1 | ∞ | 0.3 | 1.883 | 40.76 |
| 2 | 0.8359 | 0.55 | | |
| 3 | −2.339 | 0.42 | 1.883 | 40.76 |
| 4 | −5.702 | Variable | | |
| 5 | 1.354 | 0.46 | 1.58913 | 61.14 |
| 6 | 1.581 | Variable | | |
| 7(Stop) | ∞ | 0.03 | | |
| 8 | ∞ | 0.15 | | |
| 9 | 3.0599 | 0.9 | 1.7725 | 49.60 |
| 10 | −2.8105 | 1.6 | | |
| 11 | 2.439 | 1.1 | 1.48749 | 70.23 |
| 12 | −1.322 | 0.52 | 1.95906 | 17.47 |
| 13 | −3.071 | 0.09 | | |
| 14 | ∞ | 0.8 | 1.521 | 65.13 |
| 15 | ∞ | 0.3672 | | |
| 16 | ∞ | 0.7 | 1.51633 | 64.14 |
| 17 | ∞ | 0.01 | 1.513 | 64.00 |
| 18 | ∞ | 0.5 | 1.61062 | 50.49 |
| Image plane | ∞ | | | |

-continued

Unit mm

Variable data

|  | Normal observation state | Close observation state |
|---|---|---|
| d4 | 0.16 | 0.49 |
| d6 | 0.7 | 0.37 |
| Fno | 6.025 | 6.056 |
| ω | 73.29 | 70.12 |
| IH | 1 | 1 |
| f | 1.002 | 1.004 |
| BF | −0.046 | −0.145 |
| LTL | 9.357 | |

Example 3

Unit mm

Surface data

| Surface no. | r | d | nd | vd |
|---|---|---|---|---|
| 1 | ∞ | 0.3 | 1.883 | 40.76 |
| 2 | 0.8359 | 0.55 | | |
| 3 | −2.339 | 0.42 | 1.883 | 40.76 |
| 4 | −5.702 | Variable | | |
| 5 | 1.354 | 0.46 | 1.58913 | 61.14 |
| 6 | 1.581 | Variable | | |
| 7(Stop) | ∞ | 0.03 | | |
| 8 | ∞ | 0.15 | | |
| 9 | 2.8343 | 1.15 | 1.7725 | 49.60 |
| 10 | −3.2936 | 1.35 | | |
| 11 | 2.439 | 1.1 | 1.48749 | 70.23 |
| 12 | −1.322 | 0.52 | 1.95906 | 17.47 |
| 13 | −3.071 | 0.09 | | |
| 14 | ∞ | 0.8 | 1.521 | 65.13 |
| 15 | ∞ | 0.7435 | | |
| 16 | ∞ | 0.7 | 1.51633 | 64.14 |
| 17 | ∞ | 0.01 | 1.513 | 64.00 |
| 18 | ∞ | 0.5 | 1.61062 | 50.49 |
| Image plane | ∞ | | | |

Variable data

|  | Normal observation state | Close observation state |
|---|---|---|
| d4 | 0.16 | 0.49 |
| d6 | 0.7 | 0.37 |
| Fno | 6.178 | 6.212 |
| ω | 69.94 | 67.28 |
| IH | 1 | 1 |
| f | 1.028 | 1.029 |
| BF | −0.063 | −0.168 |
| LTL | 9.734 | |

The values of conditional expressions (1-1) to (7) in example 1, example 2, and example 3 are shown below.

| | Conditional expression | Example1 | Example2 | Example3 |
|---|---|---|---|---|
| (1-1) | $|flp/f_2|$ | 0.434 | 0.426 | 0.451 |
| (1-2) | $d_{45}/flp$ | 0.680 | 0.791 | 0.631 |
| (2) | $f_{56}/flp$ | 2.886 | 2.937 | 2.779 |
| (3) | $\Sigma d/flp$ | 4.554 | 4.626 | 4.553 |
| (4) | $d_4/flp$ | 0.486 | 0.445 | 0.538 |
| (5) | $flp \times rh_1/ih^2$ | 1.954 | 1.889 | 1.952 |
| (6) | $|flp \times f_{123}|/rh_1^2$ | 1.811 | 1.829 | 2.023 |
| (7) | $flp \times rh_1/fl\_f^2$ | 1.973 | 1.889 | 1.854 |

The abovementioned objective optical system for endoscope may satisfy a plurality of arrangements simultaneously. Making such arrangement is preferable from a viewpoint of achieving a favorable objective optical system for endoscope. Moreover, combinations of preferable arrangements are arbitrary. Furthermore, regarding each conditional expression, only an upper limit value or a lower limit value of a further restricted numerical range of conditional expression may be restricted.

The embodiment and various examples of the present invention are described above. However, the present invention is not restricted to these embodiment and examples, and embodiments formed by combining arrangements of these embodiment and examples without departing from the scope of the present invention are also included the category of the present invention The present embodiment shows an effect that it is possible to provide an objective optical system for endoscope which is small-sized, and in which the optical performance is secured.

As described heretofore, the present invention is useful for an objective optical system for endoscope which is small-sized, and in which the optical performance is secured.

What is claimed is:

1. An objective optical system for endoscope consisting of, in order from an object side:
a first negative lens which is planoconcave, and of which a flat surface is directed toward the object side;
a second meniscus lens having a convex surface directed toward an image side;
a third positive meniscus lens having a convex surface directed toward the object side;
a fourth positive lens; and
a cemented lens in which a fifth positive lens and a sixth negative lens are cemented, wherein
focusing is carried out by the third positive meniscus lens moving along an optical axis, and
the following conditional expressions (1-1) and (1-2) are satisfied:

$$0.41 < |flp/f_2| < 1 \quad (1\text{-}1), \text{ and}$$

$$0.55 < d_{45}/flp < 1 \quad (1\text{-}2)$$

where,
flp denotes a focal length of the fourth positive lens,
$f_2$ denotes a focal length of the second meniscus lens, and
$d_{45}$ denotes an air space between the fourth positive lens and the fifth positive lens.

2. The objective optical system for endoscope according to claim 1, wherein the following conditional expression (2) is satisfied:

$$2.6 < f_{56}/flp < 3.8 \quad (2)$$

where,
flp denotes the focal length of the fourth positive lens, and
$f_{56}$ denotes a focal length of the cemented lens.

3. The objective optical system for endoscope according to claim 1, wherein the following conditional expression (3) is satisfied:

$$4.1 < \Sigma d/flp < 5.5 \quad (3)$$

where,
flp denotes the focal length of the fourth positive lens, and
$\Sigma d$ denotes an overall optical length of the objective optical system for endoscope.

4. The objective optical system for endoscope according to claim 1, wherein the following conditional expression (4) is satisfied:

$$0.44 < d_4/flp < 1 \qquad (4)$$

where, flp denotes the focal length of the fourth positive lens, and
$d_4$ denotes a thickness of the fourth positive lens.

5. The objective optical system for endoscope according to claim 1, wherein the following conditional expression (5) is satisfied:

$$1.8 < flp \times rh_1/ih^2 < 2.5 \qquad (5)$$

where, flp denotes the focal length of the fourth positive lens,
$rh_1$ denotes the maximum height of a light ray in a normal observation state of the first negative lens, and
ih denotes an image height.

6. The objective optical system for endoscope according to claim 1, wherein the following conditional expression (6) is satisfied:

$$1 < |flp \times f_{123}|/rh_1^2 < 2.1 \qquad (6)$$

where, flp denotes the focal length of the fourth positive lens,
$rh_1$ denotes the maximum height of a light ray in the normal observation state of the first negative lens, and
$f_{123}$ denotes a combined focal length in the normal observation state of the first negative lens, the second meniscus lens, and the third positive meniscus lens.

7. The objective optical system for endoscope according to claim 1, wherein the following conditional expression (7) is satisfied:

$$1.76 < flp \times rh_1/f1\_f^2 < 2.51 \qquad (7)$$

where, flp denotes the focal length of the fourth positive lens,
$rh_1$ denotes the maximum height of a light ray in the normal observation state of the first negative lens, and
f1_f denotes a focal length of the overall objective optical system for endoscope in the normal observation state.

* * * * *